United States Patent [19]

Maloney et al.

[11] Patent Number: 4,906,230
[45] Date of Patent: Mar. 6, 1990

[54] STEERABLE CATHETER TIP

[75] Inventors: Patrick M. Maloney, El Toro, Calif.; Matthew Hoskins, Portland, Oreg.

[73] Assignee: Baxter Travenol Laboratories, Inc., Deerfield, Ill.

[21] Appl. No.: 261,764

[22] Filed: Oct. 24, 1988

Related U.S. Application Data

[62] Division of Ser. No. 68,559, Jun. 30, 1987, abandoned.

[51] Int. Cl.⁴ .............................................. A61M 25/00
[52] U.S. Cl. ............................................ 604/95; 128/4
[58] Field of Search ................... 604/95, 96, 280, 288; 188/4–6, 348.1

[56] References Cited

U.S. PATENT DOCUMENTS

| | | |
|---|---|---|
| 3,270,641 | 9/1966 | Gosselin . |
| 3,485,237 | 12/1969 | Bedford . |
| 3,605,725 | 9/1971 | Bentov . |
| 3,665,928 | 5/1972 | Del Guercio ........................ 604/95 |
| 3,799,151 | 3/1974 | Fukaumi . |
| 4,066,070 | 1/1978 | Utsugi . |
| 4,207,872 | 6/1980 | Meiri . |
| 4,245,624 | 1/1981 | Komiya . |
| 4,280,500 | 7/1981 | Ono . |
| 4,389,208 | 6/1983 | LeVeen . |
| 4,403,985 | 9/1983 | Boretos . |
| 4,447,227 | 5/1984 | Kotsanis . |
| 4,563,181 | 1/1986 | Wijayaranthna . |
| 4,586,923 | 5/1986 | Gould . |
| 4,643,720 | 2/1987 | Lanciano . |

Primary Examiner—Stephen C. Pellegrino
Attorney, Agent, or Firm—Gordon L. Peterson; Frank J. Uxa, Jr.

[57] ABSTRACT

A catheter sized and adapted to be passed through a tortuous path into a desired location in a human medical patient's body is disclosed. This catheter includes a deflection system, such as a bellows located at or near the distal end of the catheter. The distal end portion of the catheter can be controllably deflected, relative to the remainder of the catheter, by activating, e.g., pressurizing, the deflection system. This controlled deflection allows one to easily maneuver the catheter through the tortuous path.

25 Claims, 2 Drawing Sheets

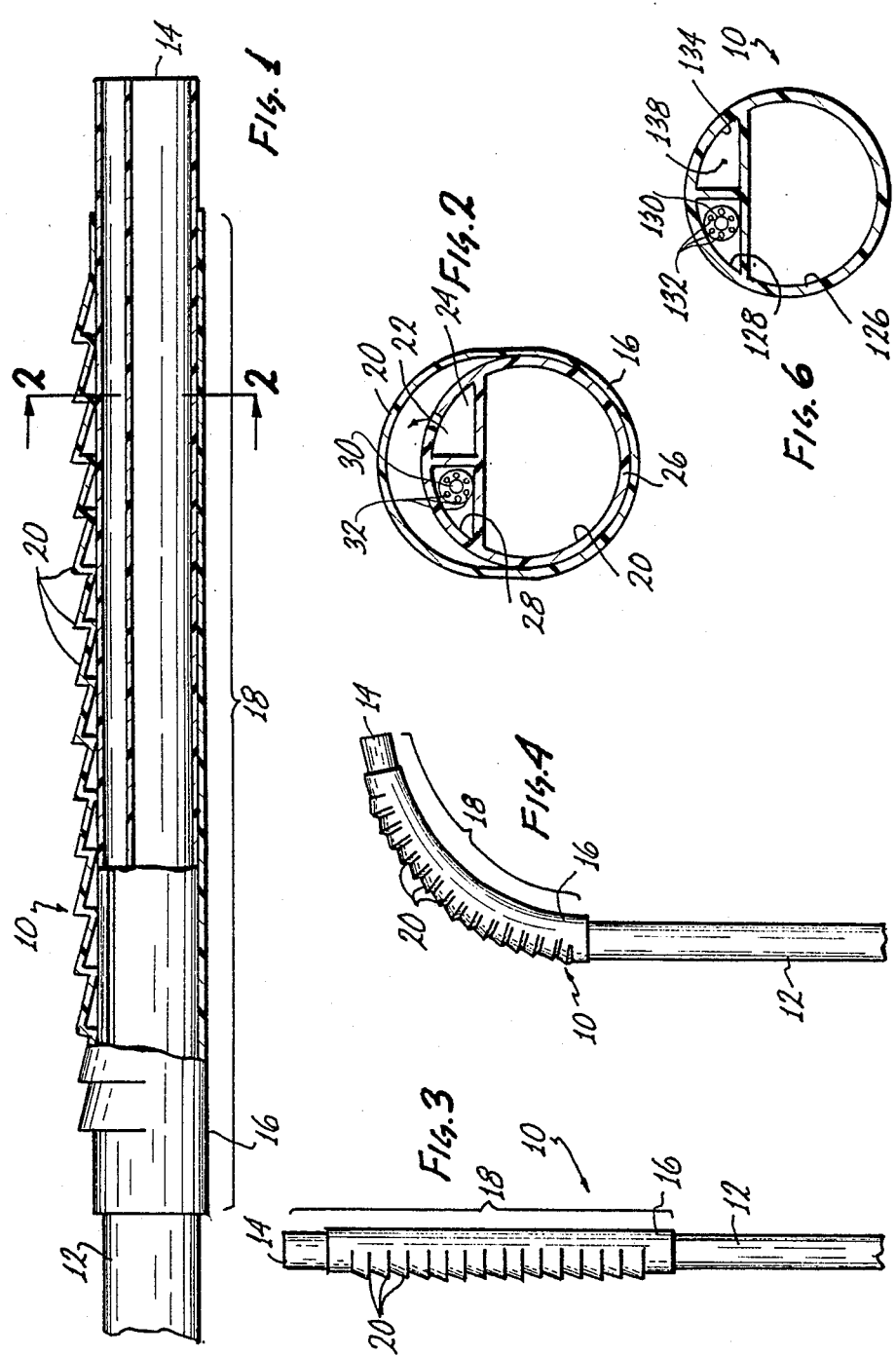

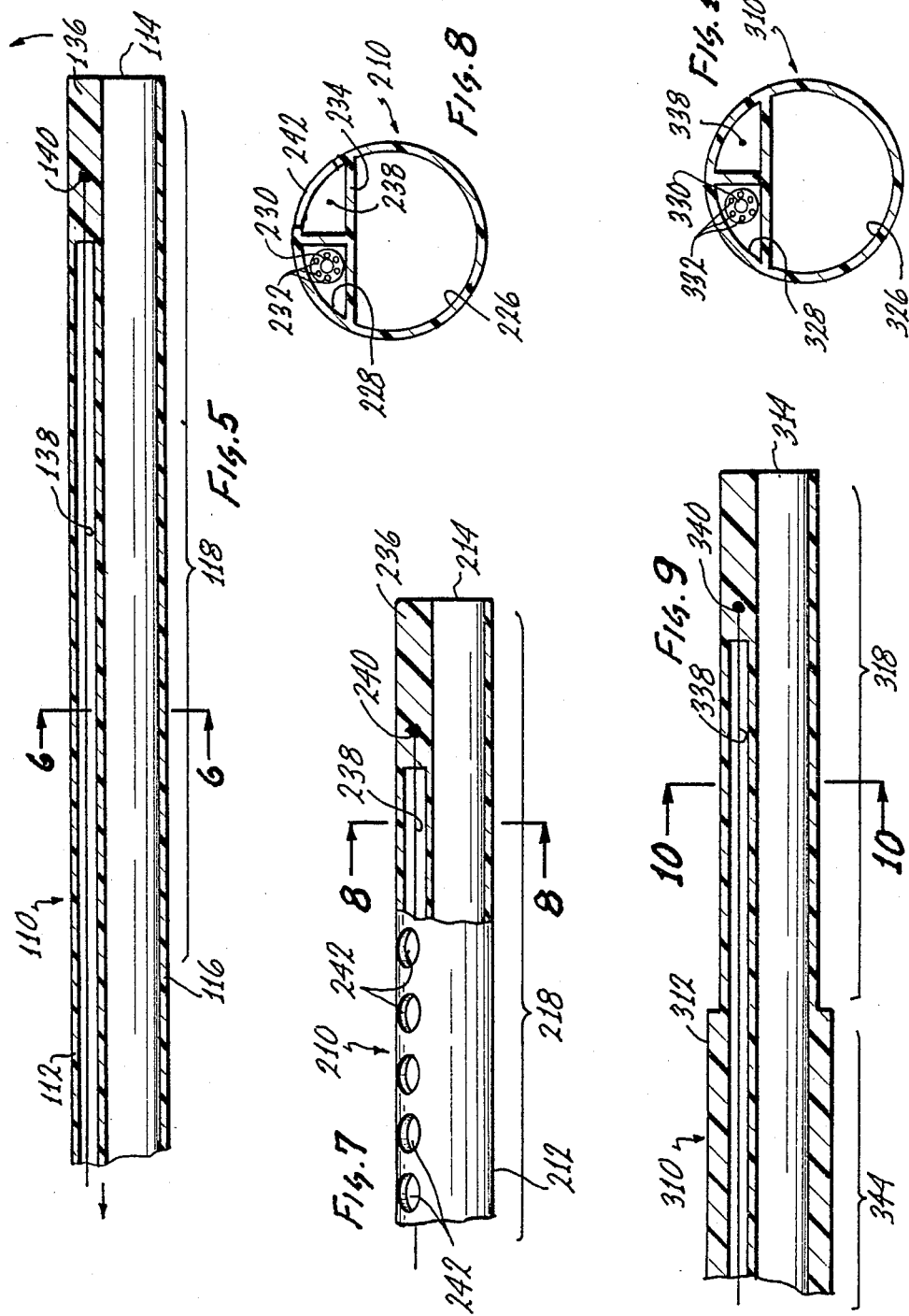

STEERABLE CATHETER TIP

This application is a division of application Ser. No. 068,559, filed Jun. 30, 1987, now abandoned.

BACKGROUND OF THE INVENTION

This invention relates to a steerable catheter for use in treating a medical patient. More particularly, the invention relates to such a catheter in which the distal end portion thereof can be deflected in a controlled manner so that the catheter can be inserted through a tortuous path to a desired location in the patient's body.

The use of various catheters is becoming increasingly important in the diagnosis and treatment of disease. However, in order to perform its function, the catheter must first be inserted into the patient's body and placed in the desired location. This often involves passing the catheter through a tortuous path in the patient's body. Examples, of such tortuous paths include the upper gastro-intestinal (G.I.) tract, and the urinary tract.

Passing a catheter through such tortuous paths has heretofore been very difficult and time consuming, adding greatly to the discomfort of the patient and the overall cost of the procedure involved. Since the distal end of a conventional catheter is not readily controllable, repeated, unsuccessful attempts to manipulate the catheter through the tortuous path are often necessary before the catheter successfully navigates the path and is properly placed in the patient's body.

In preparing this application, the following U.S. Pat. Nos. were considered: 4,447,227; 4,403,985; 4,389,208; 4,066,070; and 3,485,237. U.S. Pat. No. 4,403,985 discloses a jet controlled catheter which involves a complicated series of valves and fluid passageways. Also, the fluid used to control the movement of the catheter does enter the passage of the body containing the catheter. The presence of such fluid in the body passage may not be desirable. The other patents noted above also disclose relatively complex systems for advancing catheters.

Cook Urological Surgical Products has recently introduced a deflecting wire guide which is used through flexible or rigid ureteroscopes to help negotiate the ureter. This device involves a string attached to the distal end of the wire guide coil. The string is pulled to cause the distal end of the wire guide to deflect. The amount of deflecting force that can be applied to a guide wire coil is often insufficient to deflect a relatively much bigger and heavier catheter/guide wire composite.

A new system providing an easily and effectively steerable, e.g., manueverable, catheter would clearly be advantageous.

SUMMARY OF THE INVENTION

A new steerable catheter has been discovered. This catheter includes an elongated catheter body and a deflection means or system which is located off center with respect to the central longitudinal axis of the catheter body. The off center deflection system is capable of being activated to controllably deflect the distal end portion of the catheter body relative to the remainder of the catheter body, i.e., the body portion of the catheter body. The present system is preferably structured so that substantially no fluid used to deflect the catheter passes into the space where the catheter is located. Providing such controlled deflection in combination with coordinated insertion force or pressure results in the present catheter being steerable into the desired location in the patient's body.

The present invention provides substantial advantages. The present off center deflection system allows for easy and reliable control of the distal end of the catheter. Various embodiments of this system, e.g., as disclosed herein, are relatively simple in construction and operation. Relatively little, if any, auxiliary equipment is needed to effectively steer the catheter. Also, the present catheter is preferably structured so as to have no substantial adverse impact on the passage of the body into which it is inserted. In other words, the present catheter is preferably structured, e.g., sized, to be substantially similar in its external configuration to a conventional catheter. In summary, the present catheter includes a simple, reliable and effective deflection system which allows the catheter to be controllably steered without substantially adversely affecting the overall functioning of the catheter.

The present catheter body includes at least one, preferably more than one, lumen extending through a substantial portion of the catheter body. In one embodiment, the catheter body includes at least two lumens. The deflection system is preferably located at least partially in a lumen or in fluid communication with a lumen.

In a particularly useful embodiment, the deflection system includes a string-like element secured to the catheter body at or near the distal end portion thereof. This string-like element, e.g., a chord, suture, cable and the like, may be bonded, molded, tied or otherwise secured to the catheter body. In an especially useful embodiment, the string-like element is molded into the distal end portion of the catheter body. The string-like element is preferably located at least partially in a lumen of the catheter body. This structure avoids potential damage which might be caused to the tissue surrounding the catheter by having the string-like member located outside the catheter.

In order that the deflection system can operate more effectively, it is preferred that the distal end portion of the catheter body have increased flexibility relative to the body portion of the catheter body. Put another way, the body portion preferably has increased column strength relative to the distal end portion. This increased distal end portion flexibility can be accomplished in various ways. For example, the distal end portion can be made of a different, more flexible material than the body portion. The distal end portion can have a thinner construction, e.g., thinner sidewalls, than the body portion. If a string-like element is employed, part or parts of the lumen in which the string is located can be cut away, i.e., such part or parts of the lumen is or are absent, to provide the distal end portion with increased flexibility. A flexible bellows-like element can be located around a portion of the periphery of the distal end portion of the catheter body. This bellows element provides an increased degree of flexibility to such distal end portion.

In another embodiment, the deflection means includes a flexible bellows-like element located around a portion of the periphery of the distal end portion of the catheter body which is in fluid communication with the lumen extending through the catheter body. In this embodiment the catheter preferably includes at least two lumens, with the lumen in fluid communication with the bellows being fluid inflatable, i.e., fluid pressurizable. The bellows is preferably structured to resist fluid inflation radially from the central longitudinal axis of the catheter.

By controlling the degree of fluid pressurization in the fluid inflatable lumen, the degree of deflection of the distal end portion can be controlled.

The present catheter may be adapted to perform any suitable operative or diagnostic function. One particularly useful function such catheters can perform is that of visualization. In this embodiment, the catheter further comprises visualization means acting to provide a visualization of space at or near the distal end portion of the catheter body. The visualization means preferably includes at least one light emitting optical fiber, more preferably an array of light emitting optical fibers, and at least one imaging optical fiber. Both the light emitting optical fiber or fibers and the imaging optical fiber or fibers are preferably located substantially in a lumen of the catheter. Such optical fibers and their operation are conventional and well known is the art. Therefore, a detailed discussion of such topics is not presented here. These fibers do provide a visualization of space at or near the distal end portion of the catheter body. By activating the deflection means appropriately, one can very effectively obtain one or more visualizations of the area of the body in or near which the distal end portion of the catheter body is located. This adds greatly to the effectiveness of the visualization catheter which includes the present off-center deflection system.

Included within the scope of the present invention is a method for inserting a catheter through a tortuous path to a desired location, e.g., in the gastro-intestinal tract, the urinary tract and the like, in a patient's body. This method includes passing a catheter such as described herein through a tortuous path in a patient's body and activating the catheter's deflection system, e.g., as needed, during the passing step to facilitate inserting or placing the catheter at the desired location in the patient's body. By appropriately causing the distal end portion of the catheter to deflect at appropriate points during the insertion of the catheter, the catheter is more easily inserted and can bend or turn around portions of the tortuous path so that such path can be navigated.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a side view, partly in cross-section, of one embodiment of the present catheter.

FIG. 2 is a cross-sectional view taken along line 2—2 in FIG. 1.

FIG. 3 is a plan view of the embodiment shown in FIG. 1 where the distal tip is not deflected.

FIG. 4 is a plan view of the embodiment shown in FIG. 1 where the distal tip is deflected.

FIG. 5 is a side-view, in cross-section, of an alternate embodiment of the present catheter.

FIG. 6 is a cross-sectional view taken along line 6—6 in FIG. 5.

FIG. 7 is a side view, in cross-section, of a further embodiment of the present catheter.

FIG. 8 is a cross-sectional view taken along line 8—8 in FIG. 7.

FIG. 9 is a side view, in cross-section, of another embodiment of the present catheter.

FIG. 10 is a cross-sectional view taken along line 10—10 in FIG. 9.

DESCRIPTION OF THE DRAWINGS

Referring now to the drawings, a first catheter, shown generally at 10, includes a multi-lumen catheter body 12, a distal tip 14 and a bellows-containing collar 16, which surrounds and is adhesively secured to the distal end portion 18 of catheter body 12. The individual bellows folds 20 of collar 16 form hollow spaces with the exterior of catheter body 12. As best seen in FIG. 2, these bellows folds 20 extend around about one half of the periphery of catheter body 12, and are in fluid communication through a fluid passage 22 with an inflation lumen 24. Fluid passage 22 runs longitudinally along catheter body 12 so that all of the spaces formed by bellows folds 20 are in fluid communication with inflation lumen 24. Inflation lumen 24 runs substantially the entire longitudinal distance of catheter body 12 and terminates at the distal tip 14 of catheter body 12. Inflation lumen 24 is in fluid communication with a source of fluid pressure (not shown) which can be activated to change, e.g., increase, the fluid pressure within inflation lumen 24, as desired.

Both catheter body 12 and collar 16 are made of flexible materials, e.g., synthetic polymeric materials. Distal end portion 18 of first catheter 10 can be made of a more flexible material than the material used to make catheter body 12. Thus, distal end portion 18 may have increased flexibility relative to that portion of catheter body 12 proximally of collar 16.

As noted above, catheter body 12 includes a plurality of lumens which extend substantially the entire length of catheter body 12. One of these lumens includes a working channel 26 which may be used for various purposes, such as. infusion of fluid into the patient's body. Light lumen 28 is also included, and is used to carry an imaging optical fiber 30 surrounded by an array of light emitting optical fibers 32. First catheter 10 is useful as a visualization catheter to provide visualizations of space at or near distal tip 14. This, light emitting optical fibers 32 provide light at distal tip 14 which allows imaging optical fiber 30 to transmit image signals from at or near distal tip 14 to a position proximal catheter body 12 to produce a visualization of this space. Both imaging optical fiber 30 and light emitting optical fibers 32 are conventional in construction and operation and, therefore, are not discussed in detail here.

Inflation lumen 24 and bellows folds 20 are both located off center relative to the longitudinal axis of catheter body 12. This off-center feature allows distal end portion 18 to be deflected or bent in a predictable manner, thus providing for important control in deflecting distal end portion 18.

First catheter 10 functions as follows. When it is desired to place first catheter 10 through a tortuous path, first catheter 10 is inserted into the entrance of that path. In order to facilitate distal end portion 18 of catheter body 12 navigating the tortuous path, inflation lumen 24 is periodically subjected to controlled fluid, e.g., gas, pressurization. Such pressurization, preferably to a pressure of about 100 psig to about 150 psig, places the bellows folds 20 and. the adjacent regions of the distal end portion 18 in longitudinal tension to thereby cause distal end portion 18 to deflect in a known direction e.g., as shown in FIG. 4. This controlled deflection of distal end portion 18 allows catheter body 12 to be inserted into the "zigs" and "zags" of the tortuous path. If a straight path or portion of the path is anticipated, inflation lumen 24 is depressurized and distal end portion 18 assumes an aligned or straight configuration under the influence of its own resilience relative to the remainder of catheter body 12, as shown in FIG. 3. The amount of fluid pressurization in inflation lumen 24 determines the amount or degree of deflection of distal end portion 18.

Once first catheter 10 has been placed at the desired location in the patient's body, imaging optical fiber 30 and light emitting optical fibers 32 are activated to obtain the desired visualizations of the space around distal tip 14. Inflation lumen 24 can be fluid pressurized at the point to cause distal end portion 18 to deflect in a controlled manner so that visualizations of the entire space around distal tip 14 can be obtained, as desired.

A second catheter, shown generally in FIGS. 5 and 6 at 110, includes a number of similar components similar to the components described above with respect to first catheter 10. These similar components include a second catheter body 112, a distal tip 114, and a distal end portion 118 of catheter body 112.

Catheter body 112 is made of flexible materials, e.g., synthetic polymeric materials. Distal end portion 118 of second catheter 110 is made of a more flexible material, e.g., a more flexible plastic, than the material used to make catheter body 112 proximal of portion 118. Thus, distal end portion 118 has increased flexibility relative to that portion of catheter body 112 proximal of portion 118.

Catheter body 112 includes a plurality of lumens which extend substantially the entire length of catheter body 112. One of these lumens includes a working channel 126, while a light lumen 128 is also included and carries an imaging optical fiber 130 surrounded by an array of light emitting optical fibers 132. Each of the components of second catheter 110 noted in this paragraph is structured and functions in much the same manner as the corresponding component in first catheter 10, described above.

Second catheter 110 differs from first catheter 10 at least as follows. Catheter body 112 includes a utility lumen 134 which extends through substantially the entire length of catheter body 112 and is stopped-up at the distal end of catheter body 112 by a plug 136. A string 138, an aramid fiber, which fiber is sold by DuPont under the trademark Kevlar, is knotted at one end to form a knot 140 which is molded into plug 136, thereby permanently securing string 138 into utility lumen 134.

String 138 is situated off-center relative to the longitudinal axis of catheter body 112. This off-center feature allow distal end portion 118 to be deflected or bent in a predictable manner. This provides for important deflection control.

Second catheter 110 functions as follows. When it is desired to place second catheter 110 in a location in a patient's body by inserting second catheter 110 through a tortuous path, second catheter 110 is inserted into the entrance of the path. In order to facilitate distal en portion 118 of catheter body 112 navigating the tortuous path, string 138 is periodically pulled in a controlled manner. Such pulling places an off center axial compressive force on the distal end portion 118 to cause distal end portion 118 to deflect in a known direction. This controlled deflection of distal end portion 118 allows catheter body 112 to be inserted into the "zigs" and "zags" of the tortuous path. If a straight path or portion of the path is anticipated, the pulling pressure on string 138 is released and distal end portion 118 assumes an aligned or straight configuration relative to the remainder of catheter body 112. The amount of pulling pressure on string 138 determines the amount or degree of deflection of distal end portion 118.

Once second catheter 110 has been placed at the desired location in the patient's body, imaging optical fiber 130 and light emitting optical fibers 132 are activated to obtain the desired visualizations of the space around distal tip 114. String 138 can be pulled at this point to cause distal end portion 118 to deflect in a controlled manner so that visualizations of the entire space around distal tip 114 can be obtained, as desired.

A third catheter, shown generally in FIGS. 7 and 8 at 210, includes a number of components similar to the components described above with respect to second catheter 110. These similar components include a third catheter body 212, a distal tip 214, a distal end portion 218 of catheter body 212, a working channel 226, a light lumen 228, an imaging optical fiber 230, an array of light emitting optical fibers 232, a utility lumen 234, a plug 236, a string 238 and a knot 240. Each of the components of third catheter 210 noted in this paragraph is structured and functions in much the same manner as the corresponding component in second catheter 110, described above.

Third catheter 210 differs from second catheter 110 at least as follows. Catheter body 212 is made entirely of the same material. However, a series of holes 242 are cut into utility lumen 234. The presence of holes 242 provides distal end portion 218 with increased flexibility relative to that portion of catheter body 212 proximal to distal end portion 218. Both string 238 and holes 242 are situated off center relative to the longitudinal axis of third catheter body 212. This off-center feature allows distal end portion 218 to be deflected or bent in a predictable manner and provides for important deflection control.

Third catheter 210 functions in much the same manner as does second catheter 110, described above.

A fourth catheter, shown generally in FIGS. 9 and 10 at 310, includes a number of components similar to the components described above with respect to second catheter 110. These similar components include a fourth catheter body 312, a distal tip 314, a distal end portion 318 of catheter body 312, a working channel 326, a light lumen 328, an imaging optical fiber 330, an array of light emitting optical fibers 332, a utility lumen 334, a plug 336, a string 338 and a knot 340. Each of the components of fourth catheter 310 noted in this paragraph is structured and functions in much the same manner as the corresponding component in second catheter 110, described above.

Fourth catheter 310 differs from second catheter 110 at least as follows. Catheter body 312 is made entirely of the same material. However, the proximal portion 344 of fourth catheter body 312 has a thicker side wall than does distal end portion 318. This construction provides distal end portion 318 with increased flexibility relative to proximal portion 344 of fourth catheter body 312. String 338 is situated off center relative to the longitudinal axis of fourth catheter body 312. This off-center feature allows distal end portion 318 to be deflected or bent in a predictable manner and provides for important deflection control.

Fourth catheter 310 functions in much the same manner as does second catheter 110, described above.

In none of the embodiments illustrated in the drawings in there any fluid exiting the distal end portion of the catheter to cause the deflection of the distal end portion.

While this invention has been described with respect to various specific examples and embodiments, it is to be understood that the inventions is not limited thereto and that it can be variously practiced within the scope of the following claims.

What is claimed is:

1. A catheter comprising:
   an elongated catheter body having a body portion, a distal end portion, a central longitudinal axis and at least one lumen extending through a substantial portion of said catheter body; and
   deflection means including a bellows located at or near said distal end portion off center with respect to said central longitudinal axis and being capable of being pressurized from a fluid pressure source without passing fluid out of said distal end portion to controllably deflect said distal end portion relative to said body portion.

2. The catheter of claim 1 which further comprises visualization means located at least partially in a lumen of said catheter body and acting to provide a visualization of space at or near said distal end portion.

3. The catheter of claim 2 wherein said visualization means includes at least one light emitting optical fiber and at least one imaging optical fiber.

4. The catheter of claim 1 wherein said deflection means is located in fluid communication with said lumen.

5. The catheter of claim 4 wherein said catheter includes at least two lumens and further comprises visualization means acting to provide a visualization of space at or near said distal end portion, said visualization means being at least partially located in a lumen other than the lumen which is in fluid communication with said deflection means.

6. The catheter of claim 1 wherein said distal end portion has increased flexibility relative to said body portion.

7. The catheter of claim 1 wherein said catheter includes at least two lumens, one of said lumens being in fluid communication with said bellows.

8. The catheter of claim 7 wherein said bellows is structured to resist fluid inflation radially from said central longitudinal axis.

9. A catheter comprising:
   an elongated catheter body having a body portion, a distal end portion, a central longitudinal axis and at least one lumen extending through a substantial portion of said catheter body; and
   deflection means including bellows located around a portion of the periphery of said distal end portion in fluid communication with said lumen off center with respect to said central longitudinal axis and being capable of being pressurized for a fluid pressure relative to said body portion.

10. The catheter of claim 9 wherein said catheter includes at least two lumens and further comprises visualization means acting to provide a visualization of space at or near said distal end portion, said visualization means being at least partially located in a lumen other than the lumen which is in fluid communication with said bellows.

11. The catheter of claim 10 wherein said bellows is structured to resist fluid inflation radially from said central longitudinal axis.

12. The catheter of claim 11 wherein said visualization means includes at least one light emitting optical fiber and at least one imaging optical fiber.

13. The catheter of claim 10 wherein said visualization means includes at least one light emitting optical fiber and at least one imaging optical fiber.

14. The catheter of claim 9 wherein said bellows is structured to resist fluid inflation radially from said central longitudinal axis.

15. A method for inserting a catheter through a tortuous path to a desired location in a patient's body comprising:
   passing a catheter through a tortuous path in a patient's body, said catheter comprising an elongated catheter body having a distal end portion, a body portion, a central longitudinal axis, at least one lumen extending through a substantial portion of said catheter body, and deflection means including a bellows located at or near said distal end portion off center with respect to said central longitudinal axis and being capable of being activated to controllably deflect said distal end portion relative to said catheter body; and
   activating, without passing fluid out of said distal end portion, said deflection means during said passing to facilitate placing said catheter in a desired located in said patient's body.

16. The method of claim 14 wherein said deflection means further acts to provide increased flexibility to said distal end portion relative to said catheter body.

17. The method of claim 16 wherein said bellows is in fluid communication with a fluid inflatable lumen, and said deflection means is activated by passing fluid to said fluid inflatable lumen.

18. The method of claim 17 wherein said bellows is structured to resist fluid inflation radially from said central axis.

19. The method of claim 15 wherein said tortuous path is at least a portion of the gastro-intestinal tract of the urological tract of a patient.

20. The method of claim 15 wherein said catheter further comprises visualization means located at least partially in a lumen of said catheter body and acting to provide a visualization of space at or near said distal end portion.

21. A method for visualizing space at or near the distal end of a catheter comprising:
   inserting a catheter to a desired location in a patient's body, said catheter comprising an elongated catheter body having a distal end portion, a body portion, a central longitudinal axis, at least one lumen extending through a substantial portion of said catheter body; visualization means acting to provide a visualization of space at or near said distal end portion, and deflection means including a bellows located at or near said distal end portion off center with respect to said central longitudinal axis and being capable of being activated to controllably deflect said distal end portion relative to said catheter body;
   causing said visualization means to provide one or more visualizations of space at or near said distal end portion;

activating, without passing fluid out of said distal end portion, said deflection means to reorient said visualization means; and repeating said causing step.

22. The catheter of claim 21 wherein said deflection means further acts to provide increased flexibility to said distal end portion relative to said catheter body.

23. The method of claim 22 wherein said bellows is in fluid communication with a fluid inflatable lumen, and said deflection means is activated by passing fluid to said fluid inflatable lumen.

24. The method of claim 23 wherein said bellows is structured to resist fluid inflation radially from said central axis.

25. The catheter of claim 21 wherein said visualization means includes at least one light emitting optical fiber and at least one imaging optical fiber.

* * * * *